(12) United States Patent
Carvin et al.

(10) Patent No.: US 8,536,356 B2
(45) Date of Patent: Sep. 17, 2013

(54) PROCESS FOR PREPARING CRYSTALS BASED ON A FATTY ACID ESTER

(75) Inventors: Philippe Carvin, Lyons (FR); Christine Villard, Meyzieu (FR)

(73) Assignee: Rhodia Operations, Aubervilliers (FR)

( * ) Notice: Subject to any disclaimer, the term of this patent is extended or adjusted under 35 U.S.C. 154(b) by 250 days.

(21) Appl. No.: 12/937,926

(22) PCT Filed: Apr. 9, 2009

(86) PCT No.: PCT/EP2009/054310
§ 371 (c)(1),
(2), (4) Date: Dec. 3, 2010

(87) PCT Pub. No.: WO2009/127596
PCT Pub. Date: Oct. 22, 2009

(65) Prior Publication Data
US 2011/0071308 A1  Mar. 24, 2011

(30) Foreign Application Priority Data
Apr. 15, 2008 (FR) ..................................... 08 02069

(51) Int. Cl.
*C07C 59/147* (2006.01)
(52) U.S. Cl.
USPC ......................................................... 554/121

(58) Field of Classification Search
USPC ......................................................... 554/121
See application file for complete search history.

(56) References Cited

U.S. PATENT DOCUMENTS

| | | | | |
|---|---|---|---|---|
| 4,486,334 A | * | 12/1984 | Horiuchi et al. | ................. 516/77 |
| 4,565,647 A | | 1/1986 | Llenado | |
| 6,306,916 B1 | | 10/2001 | Ansmann et al. | |
| 2004/0234566 A1 | * | 11/2004 | Qiu et al. | ..................... 424/401 |

FOREIGN PATENT DOCUMENTS

| | | |
|---|---|---|
| CA | 2103578 | 1/1992 |
| DE | 3617306 A1 | 5/1986 |
| DE | 4103551 A1 | 2/1991 |
| DE | 4103551 A1 * | 2/1991 |
| DE | 19511571 A1 | 3/1995 |
| EP | 581193 A1 * | 7/1993 |
| EP | 0581193 A2 | 7/1993 |
| EP | 1123730 A1 * | 8/2001 |
| EP | 1123730 A2 | 8/2001 |
| EP | 1384502 A1 * | 7/2003 |
| EP | 1384502 A1 | 7/2003 |
| WO | WO 9213512 | 8/1992 |
| WO | WO 9503782 | 2/1995 |
| WO | WO 9503782 A1 * | 2/1995 |

* cited by examiner

*Primary Examiner* — Deborah D Carr
(74) *Attorney, Agent, or Firm* — Hunton & Williams

(57) ABSTRACT

The present invention relates to an improved process for preparing a fluid concentrated ingredient based on crystals based on a fatty acid ester, and also to the use of this fluid concentrated ingredient.

17 Claims, 2 Drawing Sheets

PROCESS FOR PREPARING CRYSTALS BASED ON A FATTY ACID ESTER

CROSS-REFERENCE TO RELATED APPLICATIONS

This application is the U.S. National Phase of International Application Number PCT/EP2009/054310 filed on Apr. 9, 2009, which claims priority to French Application No. FR 0802069 filed Apr. 15, 2008, both of which are incorporated by reference herein in their entireties.

FIELD OF THE INVENTION

The present invention relates to an improved process for preparing a fluid concentrated ingredient based on crystals based on a fatty acid ester, and also to the use of this fluid concentrated ingredient.

BACKGROUND

Crystals of fatty acid esters, for example crystals of ethylene glycol distearate (EGDS), are products commonly used in cosmetic formulations, as agents for affording a certain amount of pearlescence and/or as thickeners and/or stabilizers. These crystals may be formed during the preparation of the cosmetic composition. However, for practical and economic reasons, they are often sold in the form of ready-to-use fluid concentrated ingredients, intended to be mixed with the other ingredients of the cosmetic formulation.

Processes for preparing fluid concentrated ingredients based on fatty acid esters are thus known. These processes are based on solidification of a compound based on a fatty acid ester by cooling an emulsion of the said compound, which is melted in water in the presence of surfactants. For the same emulsion, the properties of the crystals generated may depend on the cooling conditions. This step is conventionally performed in stirred reactors such as stirred tanks. Typically, the emulsion filling the tank is placed in contact with cold walls, for example via jacketed tank techniques.

For example, document DE 3617306 (Henkel) describes a process for preparing products based on a fatty acid ester in which a heated emulsion based on the fatty acid ester is cooled slowly, without flowing.

Documents DE 19511571 and U.S. Pat. No. 6,306,916 (Henkel) describe a process for preparing products based on a fatty acid ester, in which a heated emulsion based on the fatty acid ester is cooled slowly, without flowing.

Document EP 581193 (Hoechst) describes a process for preparing products based on a fatty acid ester, in which a heated emulsion based on a fatty acid ester is cooled slowly. The cooling is indicated as being able to be performed at about 0.5° C. per minute.

Document WO 9503782 (ICI) describes a process for preparing products based on a fatty acid ester, in which a heated emulsion based on a fatty acid ester is cooled slowly. The cooling is indicated as being able to be performed at up to about 0.25° C. per minute (15° C. per hour).

Document U.S. Pat. No. 4,486,334 (Lion) describes a process for preparing products based on a fatty acid ester, in which a fatty acid ester in the form of liquid crystals dissolved with a surfactant is cooled slowly. The cooling method is not indicated. Such a process is relatively impractical and is not modulable since it depends greatly on the capacity to form liquid crystals as a function of the surfactants.

Documents DE 4103551, WO 9213512, CA 2103578 and EP 0570398 (Henkel) describe a process for preparing products based on a fatty acid ester, in which a heated emulsion based on the fatty acid ester is cooled slowly, without flowing.

The homogeneity and kinetics of the cooling process are especially linked to the stirring conditions in the reactor. The slower the conditions of stirring of the medium, the longer and less homogeneous the cooling.

The cooling behaviour of the stirred emulsion as a whole may prove to be difficult without significant degradation of the optical properties of the concentrate. In this case, it is necessary to perform part of the cooling in the absence of any stirring to obtain concentrates of high pearlescence. This constraint induces extrapolation difficulties during industrialization of the process, and significantly impairs the production efficiency. For example, under standard cooling conditions, the industrial use of 10 to 25 $m^3$ reactors may require from one to several days to complete this operation. Such times reveal low production efficiency. In parallel, for an equivalent formulation, the properties of the concentrates obtained industrially are generally poorer than those acquired at the laboratory scale.

There is a need for improved processes, which can satisfy at least one of the difficulties or one of the expectations stated above.

SUMMARY OF THE INVENTION

To this end, the invention proposes a process for preparing a fluid concentrated ingredient comprising crystals based on a fatty acid ester, comprising the following steps:
step a) preparing an emulsion comprising water, a compound based on a fatty acid ester, and surfactant(s), the said emulsion being at a temperature above the melting point of the compound based on the fatty acid ester,
step b) cooling the emulsion to a temperature below the melting point of the compound, so as to form the crystals, by using at least one phase of cooling by introducing a stream of the emulsion and flowing in a cooling device that allows stirring of the stream generated by its own flow,
step c) recovering downstream of the cooling device a stream of a fluid comprising the crystals and the surfactant(s),
step d) optionally performing additional cooling of the stream,
step e) optionally adding other compounds to the fluid and/or diluting the fluid and/or mixing the fluid,
step f) recovering the fluid concentrated ingredient.

The invention also relates to uses of the products obtained in foaming formulations, especially in cosmetic formulations, typically by mixing with the other ingredients of these formulations. The invention also relates to a process for preparing such formulations, typically involving a phase of preparing the fluid concentrated ingredient, followed by a phase of mixing with the other ingredients.

The process especially makes it possible to afford at least one of the following improvements:
  improved production efficiency
  greater production regularity, especially in terms of optical properties
  greater ease of extrapolation to the industrial scale of operating conditions, of process data, of compositions, and of applicative properties (for instance the optical properties) obtained at the laboratory scale
  great ease of industrialization.

In addition, the implementation of the process makes it possible to determine whether the fluid concentrated ingredients prepared at the laboratory scale by the process of the invention can be similarly prepared at the industrial scale. With the aid of the processes of the prior art it may prove very long and very difficult, or even impossible, to industrialize fluid concentrated ingredients tested at the laboratory scale.

DEFINITIONS

In the present patent application, the term fluid concentrated ingredient means a composition comprising at least 5% by weight of crystals, preferably at least 10% by weight, preferably less than 35% by weight, typically from 15% to 30% by weight, for example from 15% to 18% or from 18% to 22%, or from 22% to 26%, or from 26% to 30%. The ingredient is usually intended to be used for the preparation of cosmetic formulations such as shampoos, hair conditioners or shower gels, comprising other ingredients, and more diluted as crystals. The term "fluid concentrated ingredient" is thus especially used as opposed to finished cosmetic formulations. The fluid concentrated ingredient may thus be termed a cold pearl concentrate.

The term compound "based on fatty acid ester" means a compound or a composition comprising at least 75% by weight of a fatty acid, and optionally other compounds.

Figure 1:
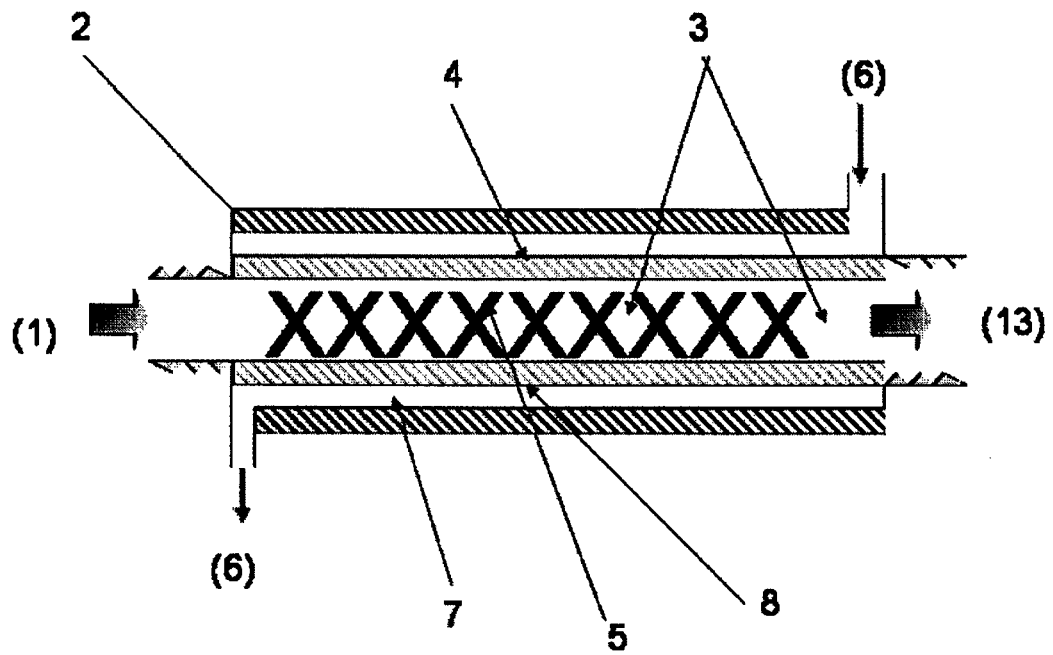
FIG. 1 shows an embodiment of a cooling device that may be used, alone or as a module, for the implementation of step b).

In the figures, the numbers in parentheses indicate the material streams and the numbers without parentheses indicate constituent components of devices.

DETAILED DESCRIPTION OF PREFERRED EMBODIMENTS

Compound Based on Fatty Acid Ester

The compound based on fatty acid ester is a compound that is solid at room temperature, preferably at a temperature of 25° C. It may especially be a compound whose melting point is greater than 30° C., preferably greater than 40° C. and preferably greater than 50° C.

The fatty acid ester on which the crystals are based may especially be an ester of a fatty acid with a diol or a polyol of formula (I) below:

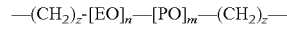
[R—COO—]$_x$-A-[-OH]$_y$    (I)

in which:
R is a saturated or unsaturated, linear or branched $C_{13}$-$C_{21}$ and preferably $C_{15}$-$C_{21}$ hydrocarbon-based group,
A is a hydrocarbon-based group, optionally interrupted with one or more heteroatoms, of valency x+y,
x is an average number between 1 and 5,
y is an average number between 0 and 5,
x+y is an average number between 1 and 10 and preferably between 2 and 5.

In the present patent application, an average number may denote a whole number or a decimal number. In the present patent application, the expression "between X and Y" includes the limits X and Y.

If y is other than 0, this means that it is a partial ester. If y=0, this means that it is a fully esterified compound. For example, if x+y=2, y=0 and x=2, it is a diester (fully esterified).

The group A is a group in which the compound of formula A-(—OH)$_{x+y}$ is a diol or a polyol. It may especially be a diol such as ethylene glycol, or a polyol such as glycerol.

Advantageously:
A is a divalent group (x+y=2; A-(—OH)$_{x+y}$ is a diol), and y=0.

The group A may especially have the following formula:

—(CH$_2$)$_z$-[EO]$_n$—[PO]$_m$—(CH$_2$)$_z$— in which:
z, which may be identical or different, is an integer from 1 to 10,
EO is an optional ethylene oxide group, and n is an average number between 0 and 100 and preferably from 0 to 10, and
PO is an optional propylene oxide group, and m is an average number between 0 and 100 and preferably from 0 to 10.

If one of the groups EO and/or PO is present, the compound of formula A-(—OH)$_2$ may be a product of (poly)ethoxylation and/or of (poly)propoxylation, or of condensation of ethylene glycol and/or of propylene glycol.

Preferably, the group A comprises no EO and/or PO groups, and it is a $C_1$-$C_{10}$ and preferably $C_2$-$C_4$ alkylene group. The group A may especially be a methylene, ethylene, propylene or butylene group or a mixture of these groups.

The group R is a hydrocarbon-based group, for example a saturated or unsaturated, linear or branched $C_{13}$-$C_{21}$ and preferably $C_{15}$-$C_{21}$ alkyl group. It is an alkyl group corresponding to a $C_{14}$-$C_{22}$ and preferably $C_{16}$-$C_{22}$ fatty acid of formula R—COOH. These fatty acids and alkyl groups are known. They are generally derivatives of plant oils. They may be present as mixtures. If they are mixtures, all the groups are included in the definition, irrespective of the number of carbon atoms, if the group (or the corresponding acid) that is predominant in weight amount (relative and preferably absolute majority, preferably at least 75%) satisfies the definition. It is common to reduce the denomination to the group (or the corresponding acid) to the predominant group (or acid).

The group R may especially correspond to a $C_{14}$ or $C_{16}$ or $C_{18}$ or $C_{22}$ fatty acid, for instance myristic, palmitic, stearic, oleic, erucic or behenic acid. Preferably, the group R—COO— corresponds to a $C_{18}$ fatty acid, preferably stearic acid.

It is possible, particularly advantageously, to use a compound based on ethylene glycol distearate (EGDS). The term compound "based on ethylene glycol distearate" means a compound or a composition comprising at least 75% by weight of ethylene glycol distearate, and optionally other compounds, especially ethylene glycol monostearate (EGMS). Unless otherwise mentioned or specified hereinbelow, especially as regards the presence of other compounds, the term ethylene glycol distearate or the acronym EGDS will denote a compound based on ethylene glycol distearate. According to one particular embodiment, the fatty acid ester comprises at least 80% by weight of ethylene glycol distearate, and optionally ethylene glycol monostearate. It may especially comprise:
from 80% to 99%, preferably from 80% to 90% and preferably about 85% by weight of ethylene glycol distearate, and
from 1% to 20%, preferably from 10% to 20% and preferably about 15% by weight of ethylene glycol monostearate.

Surfactant System

The process of the invention uses at least one surfactant. The surfactant(s) especially allow(s) formation of the emulsion. Reference may be made hereinbelow to a "surfactant system", whether a single surfactant or several surfactants is/are used.

The surfactant system may especially comprise a nonionic surfactant and/or an anionic surfactant. It is not excluded for it to comprise at least one amphoteric surfactant such as betaines (for example alkyldimethylbetaines or alkyldimethylamidoalkylbetaines) or imidazoline derivatives (for example alkylamphoacetates or alkylamphodiacetates). Surfactants that may be used are listed elsewhere later, as ingredients of the formulations. As regards the anionic and/or nonionic surfactant(s), it may be, for example, a case of an optionally sulfated ethoxylated fatty alcohol, for instance an ethoxylated fatty alcohol (nonionic surfactant) or a sulfated ethoxylated fatty alcohol (nonionic surfactant). It is mentioned that if the surfactant is an anionic surfactant, for example a sulfated ethoxylated fatty alcohol, it is generally in the form of a salt, for example a sodium or ammonium salt.

According to one embodiment, the surfactant system comprises:
  a nonionic surfactant, preferably an ethoxylated fatty alcohol, and
  optionally another surfactant, preferably chosen from anionic surfactants, amphoteric surfactants, and nonionic surfactants other than the ethoxylated fatty alcohol, and mixtures thereof.

According to another embodiment, the surfactant system comprises:
  an anionic surfactant, preferably a sulfated ethoxylated fatty alcohol, and
    another surfactant, preferably chosen from nonionic surfactants, amphoteric surfactants, and anionic surfactants other than the sulfated ethoxylated fatty alcohol, and mixtures thereof.

Among the ethoxylated fatty alcohols (nonionic surfactants), mention is made more particularly of compounds in which the fatty alcohol is saturated or unsaturated, linear or branched, and of $C_6$-$C_{22}$, preferably $C_8$-$C_{20}$ and preferably $C_{10}$-$C_{14}$, especially lauryl alcohol. It is pointed out that the fatty alcohols are generally mixtures derived from plant products or petroleum fractions. The number of carbon atoms may be an average number or the carbon number of the predominant species. These fatty alcohols are ethoxylated. The number-average number of ethoxy units may be from 1 to 25 and preferably from 5 to 9.5. The ethoxylated fatty alcohols that are particularly advantageous are ethoxylated $C_{10}$-$C_{14}$ fatty alcohols, in which the number-average number of ethoxy units is from 5 to 9.5 and preferably from 5 to 9, for example 7 or 9.

The anionic surfactant may be chosen, for example, from saturated or unsaturated, linear or branched, ethoxylated and sulfated $C_{10}$-$C_{14}$ alcohols. It may be, for example, a tridecyl alcohol, which is preferably branched and ethoxylated from 2 to 10 times, for example ethoxylated 3 times, and sulfated. By way of example, mention is made of Rhodapex EST 30 sold by Rhodia (INCI: sodium trideceth-3 sulfate).

The amphoteric surfactant may be chosen especially from alkylamidopropylbetaines, for instance cocamidopropylbetaine, and/or imidazoline derivatives, for instance alkylamphoacetates or alkylamphodiacetates, especially lauroamphoacetate or diacetate or cocoamphoacetate or diacetate.

Fluid Concentrated Ingredient

Advantageously, the fluid concentrated ingredient comprises:
  at least 5% by weight, preferably at least 10%, preferably at least 15% and usually not more than 30% by weight of crystals
  at least 2.5% by weight, preferably at least 5%, preferably at least 10% by weight and usually not more than 25% by weight of surfactant(s).

The amounts of fatty acid ester and of surfactant(s) used may be adjusted in consequence during the implementation of the process. It is not excluded to effect, at the end of the process or thereafter, dilutions by adding water or other ingredients.

The fluid concentrated ingredient may especially comprise additives such as preserving agents (generally in minor amounts, for example about 0.1% by weight), buffers, stabilizers and agents for modifying the optical properties.

The fluid concentrated ingredient may have a viscosity from 10 to 10 000 Pa·s, for example from 100 or 500 to 5000 Pa·s at 20° C., at a shear rate of 0.1 $s^{-1}$, measured using a plate/plate flow rheometer such as the Rheometrics® ARES rheometer equipped with a 50 mm spindle.

Process

During step a), an emulsion is prepared comprising water, a compound based on a fatty acid ester, and surfactant(s), the said emulsion being at a temperature above the melting point of the compound based on the fatty acid ester. Step a) may be performed in a known manner, by any method for forming an emulsion at a temperature above the melting point of the compound based on the fatty acid ester. The process may especially be performed by melting the fatty acid ester and by subsequent or simultaneous emulsification in the presence of the surfactant system.

According to one particular embodiment, step a) comprises the following steps:
a1) preparing a dispersion comprising water, solid particles based on the fatty acid ester, and surfactant(s),
a2) heating the dispersion so as to liquefy the particles based on the fatty acid ester.

Step a) may especially be performed in batch mode, semi-continuously or continuously, preferably in a tank, for example a stirred tank (11).

The temperature of the emulsion before the cooling step b) is typically greater than or equal to 1° C. higher, preferably 5° C. higher and preferably 10° C. higher than the melting point of the fatty acid ester. In the case of EGDS, the process is preferably performed at a temperature of greater than or equal to 55° C., preferably greater than or equal to 60° C., preferably from 55° C. to 70° C., and preferably from 60° C. to 70° C. or 65° C.

During step b), the emulsion is cooled to a temperature below the melting point of the compound, so as to form the crystals. This step comprises a cooling phase by introducing a stream of the emulsion (1) and flowing in a cooling device (2) that allows stirring of the stream generated by its own flow. All or part of the cooling performed during step b) may be performed with the aid of the cooling device. It is noted that part of the cooling may be performed via a chilling operation, upstream of the cooling device, in the cooling device, or even downstream. Step b) may especially comprise:
  optionally a chilling operation, upstream of the cooling device or in the cooling device, in which a chilling fluid is mixed with the stream, and/or
  optionally an optional seeding operation, in which a seeding fluid comprising crystals based on a compound based on a fatty acid ester is mixed with the stream.

Details regarding the chilling and/or seeding operations are given later.

To introduce a stream of the emulsion, the emulsion obtained in step a) can especially be withdrawn continuously to submit it downstream of the cooling step b). The process may be performed, for example, using a pump (12).

During step b), a stream of matter is made to flow into the flow device and this stream is cooled. The temperature at the point of introduction of the emulsion is thus higher than the temperature at the outlet point. In the flow device, the stream of matter undergoes a transformation, from an emulsion to a fluid comprising crystals, at the outlet of the flow device. Step b) is typically performed continuously.

The cooling performed during step b) is preferably of at least 5° C. and preferably at least 10° C. The cooling phase performed in the flow-cooling device is preferably of at least 5° C. and preferably at least 10° C.

The flow device typically has a flow zone (3) delimited by walls known as confinement walls (4). These walls delimit the space in which the stream flows. The flow zone may typically be inside a tubular device whose cross section may be of varied shape, for example round, square, rectangular or oval. The tube of the tubular device may constitute all of the confinement walls, or part of the confinement walls.

During step b), the stream that flows is subjected to stirring generated by the flow itself. The simple fact of flowing may produce the stirring. Preferably, stirring is produced by means of flow obstacles (5). These obstacles are typically provided inside the flow zone. These obstacles are preferably static. However, it is not excluded to produce additional stirring with the aid of mobile devices such as mobile stirrers. According to one advantageous embodiment, the obstacles represent a volume of at least 1%, for example from 1% to 5% or from 5% to 10%, or from 10% to 15%, or from 15% to 20%, or from 20% to 25%, or from 25% to 30%, or from 30% to 40%, or from 40% to 50%, or from 50% to 75%, of the volume of the flow zone.

The static or non-static obstacles may especially be geometrical inserts of varied shapes. The obstacles may also be constituted of an assembly of flow-vein separators and/or collectors. Cooling inserts may also be used as obstacles inside the flow zone.

The cooling of step b) may be performed via any suitable means. Such means are known to those skilled in the art. A cooling fluid may especially be used. Such cooling operations and suitable devices are known to those skilled in the art. It is especially possible to use tube exchangers, multitube exchangers, coil exchangers, plate exchangers or exchangers of Sulzer® Mixer Reactor (SMR®) type.

The cooling step b) may be effected, for example, by a cooling fluid (6) circulating in a cooling circuit (7). The cooling circuit is typically delimited by walls, known as cooling walls (8), at least part of which is in contact with the stream. The parts of walls in contact with the stream may be referred to as delimiting a cooling zone. It is noted that the confinement walls and the cooling walls may, over at least a part, constitute a common wall separating the flow zone from the cooling circuit, i.e. separating the stream from the cooling fluid. It is noted that these may be walls or parts of walls of the same component or of several components in contact (for example bonded, welded or fitted) onto the walls or parts of walls. In the embodiment shown in FIG. 1, the confinement walls (4) and cooling walls (8) are one and the same.

Figure 3:
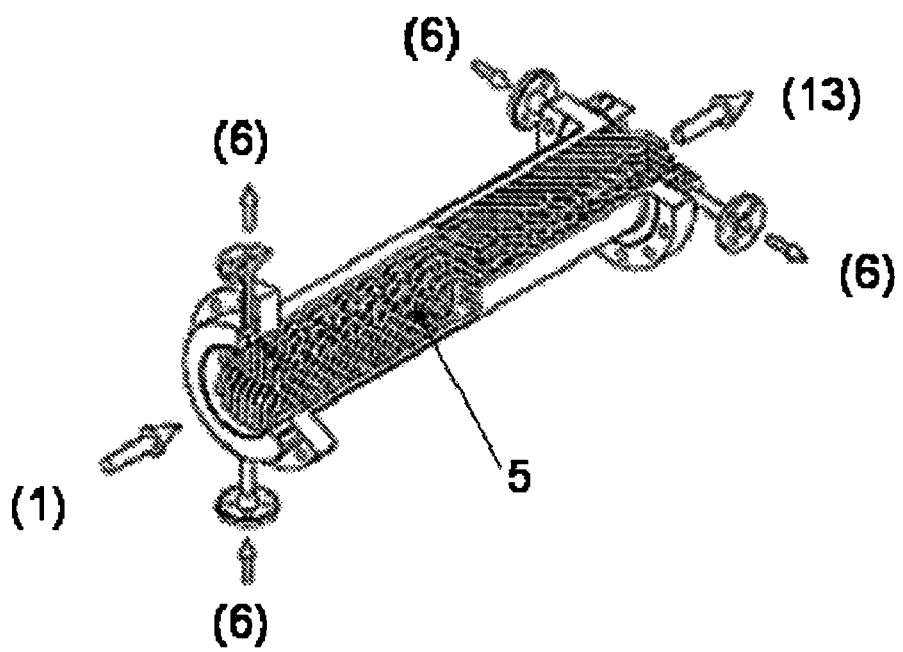
FIG. 3 shows an embodiment of the cooling device using an exchanger of Sulzer® Mixer Reactor (SMR®) type.

According to a first embodiment, the cooling circuit is placed inside the flow zone, the circuit constituting obstacles to the flow. One particular variant of this embodiment is illustrated with the aid of FIG. 3. For the implementation of this embodiment, exchangers of Sulzer® Mixer Reactor (SMR®) type may especially be used.

According to a second embodiment, the cooling circuit is placed outside the flow zone.

According to one variant of the second embodiment, the flow zone may be constituted, for example, of at least one tubular pipe constituting the confinement walls, provided on the inside with a static mixer, at least part of the confinement walls constituting a common wall with at least part of the cooling circuit. The cooling device may, for example, be a jacketed tube exchanger, in which the cooling circuit is a tubular circuit inside which is placed an inner tubular pipe in which the stream flows. Such a variant is illustrated in FIG. 1.

In one particular embodiment, use is made of a succession of cooling circuits in which flows a succession of cooling fluids at equal or variable, for example increasing or decreasing, introduction temperatures. Such an embodiment makes it possible to control and/or vary the cooling profile throughout the flow.

Figure 2:
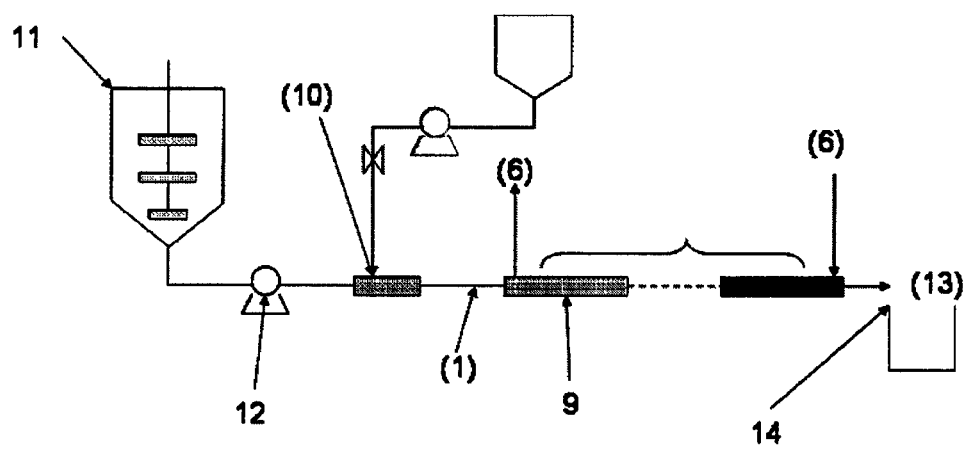
FIG. 2 is a block diagram of a particular embodiment of the process, in which chilling is performed, and in which steps d) and e) are not performed.

In one particular embodiment, the cooling device of step b) is constituted of a succession of modules (9), constituting cooling devices as described above. FIG. 2 illustrates such a particular embodiment. The module (9) may be a device as illustrated by FIG. 1.

In one particular embodiment, which is optional, during step b), chilling is performed by mixing the stream with a cold chilling fluid (10), at a temperature below or equal to the temperature of the stream at the point at which mixing is performed, preferably below or equal to the melting point of the compound based on a fatty acid ester. This mixing may be performed upstream of the flow device and/or of the flow zone and/or of the zone in contact with the cooling circuit, or at a point of the flow located on the first quarter, preferably the first eighth, preferably the first sixteenth, of the flow device and/or of the flow zone in the cooling device, for example of the cooling zone. The chilling fluid may especially be at a temperature of less than or equal to 25° C. The chilling fluid may be pure water or water comprising additives.

The chilling fluid may comprise, as primer or seed, crystals based on the compound based on the fatty acid ester. The chilling fluid may be part of the fluid recovered from step c), d) or e). The priming or seeding may facilitate the appearance of the crystals, and/or promote the production of certain crystalline forms, and thus facilitate the control of the optical properties obtained. The use of a chilling fluid is illustrated in FIG. 2.

Similarly, seeding may be performed by mixing the stream with a seeding fluid at a temperature not below or equal to the melting point of the compound based on a fatty acid ester. This mixing may be performed upstream of the flow device and/or of the flow zone and/or of the zone in contact with the cooling circuit, or at a point of the flow located on the first quarter, preferably the first eighth, preferably the first sixteenth, of the flow device and/or of the flow zone in the cooling device, for example of the cooling zone. The seeding fluid comprises, as primer or seed, crystals based on the compound based on the fatty acid ester. The seeding fluid may be part of the fluid recovered after step c), d) or e). The priming or seeding may facilitate the appearance of the crystals, and/or promote the production of certain crystalline forms, and thus facilitate the control of the optical properties obtained.

By convention in the present patent application, if a fluid comprising crystals is mixed, this fluid is referred to as a chilling fluid or as a seeding fluid, depending on the temperature.

It is mentioned that the cooling device may especially be equipped with probes for measuring the temperature and/or pressure of the stream and/or the temperature of the heat-exchange fluid. Such probes may especially allow the process to be controlled.

It has been observed that the implementation of step b) does not cause any blocking or shielding in the flow device, especially in the presence of static mixers.

Preferably, during steps a) and b), amounts of compound based on fatty acid ester and of surfactant(s) as follows are used:

an amount of compound based on fatty acid ester such that the product recovered in step c) comprises at least 5%, preferably at least 10% and preferably at least 15% by weight of fatty acid ester, an amount of surfactant(s) such that the product recovered in step c) comprises at least 2.5%, preferably 5% and preferably at least 10% by weight of surfactant(s).

According to one particular embodiment:

step a) is performed continuously, in batch mode or sequentially, and step b) is performed continuously.

After step b), during step c), a stream of a fluid (13) comprising the crystals and the surfactant(s) is recovered downstream of the cooling device. It may be a stream at room temperature, or a stream that is still hot. In this case, an additional step d) of cooling of the fluid may be performed. Such a step d) may be performed in a device with flow, continuously, or in a device without flow, statically, in batch mode or semi-continuously. Step d) may especially be performed in a tank, which may be stirred, by leaving to cool to room temperature, or by controlling the cooling. The tank may be cooled with or without cooling means such as jacketed cooling circuits and/or internal coils. The additional cooling of step d), after formation of the crystals, is less critical for the properties of the fluid concentrated ingredient to be prepared. It may be performed without affecting the production efficiency and/or the properties.

The fluid comprising the crystals and the surfactant(s), recovered in step c) and/or step d), may constitute the desired fluid concentrated ingredient. According to one embodiment, the composition of the fluid may be adjusted so as to obtain the desired fluid concentrated ingredient. To this end, an optional step e) may be performed, in which other compounds are added to the fluid and/or the fluid is diluted and/or mixed. During step e), the composition of the fluid concentrated ingredient may thus be adapted to the final formulation for which it is intended. Step e) may especially be performed in a tank, preferably with stirring. During step e), water or solvents, preserving agents, pH regulators, optical-property modifiers, stabilizers or suspensions, other surfactants (or adjustment of the concentration of the surfactants already present) or dispersants may especially be added.

It is mentioned that steps d) and e) may be performed simultaneously or subsequently, in the order d) and then e) or e) and then d).

It is pointed out that when steps d) and e) are not performed, steps c) and f) are one and the same.

During steps c) and/or f), it is possible, for example, to recover the stream and/or the concentrate in a tank and/or in a container (14) for transportation.

The process of the invention especially makes it possible to prepare fluid concentrated ingredients that have excellent and stable pearlescence and opacity properties.

Surprisingly, and without wishing to be bound to any theory, the implementation of step b) made it possible to conclude that it was possible for the cooling of the emulsion not to be limited by the heat-exchange capacities, but could be controlled by the crystallization kinetics. This especially makes it possible to determine more easily if the fluid concentrated ingredients prepared at the laboratory scale have feasibility at the industrial scale, and thus if their properties can be conserved on passing to the industrial scale.

Formulations Comprising the Fluid Concentrated Ingredient

The fluid concentrated ingredients obtained via the process of the invention may be used in formulations also comprising other ingredients. These are preferably consumer product formulations. They may especially be cosmetic formulations or household maintenance formulations. These formulations may especially be foaming formulations. They may be, for example, washing-up or dishwasher products. They may also be products for cleaning hard surfaces, for example for cleaning floors or toilets. They may also be hair-cleansing, haircare or hair-shaping formulations, for example shampoos or hair conditioners, or skin-cleansing or skincare formulations, for example shower gels, hygiene products or makeup-removing products. In such formulations, the crystals may especially be used as agents for modifying the visual perception of the formulations (especially glossy and/or opaque and/or pearlescence appearance), and/or as agents for modifying the appearance of the hair (especially shiny and/or opaque and/or pearlescence appearance) and/or as agents (for example stabilizers) for promoting the suspension of solid or liquid particles (emulsions). It may especially be a case of a use as an agent for modulating gloss and opacity, preferably affording a substantial glossy and opaque nacreous effect with reflections of several colours.

The amount of fluid concentrated ingredient used may be such that the amount of crystals included in the formulation is less than 5% by weight and typically from 1% to 4% by weight.

Besides the crystals introduced in the form of a fluid concentrated ingredient, the formulations may comprise any ingredient generally used in the fields of application under consideration. Thus, the formulations may especially comprise surfactants. For cosmetic formulations, mention is made especially of:

cosmetically acceptable vectors, especially aqueous, alcoholic or hydroxyalcoholic vectors, nonionic, anionic, cationic or amphoteric (including zwitterionic) surfactants, and mixtures thereof, especially those mentioned as being able to be present in the fluid concentrated ingredient, active agents, in dissolved form or in the form of solid or liquid particles, for example antidandruff particles, and mineral or organic UV-screening agents, natural, mineral or plant oils, derivatives thereof or synthetic oils, especially silicones. The silicones may especially be in dissolved or dispersed form, especially dimethicones, amodimethicones, dimethiconols, cationic silicones, and silicones comprising polyethylene glycol blocks, in the form of oils, or of an emulsion with a mean size of greater or less than 2 μm, or in the form of microemulsions smaller than 0.15 μm, or even in dissolved form. In the case of an emulsion, the emulsification may be performed in situ or beforehand. The viscosity of the silicones may be, for example, less than 50 000 cP, or between 50 000 and 200 000 cP, or greater than 200 000 cP, conditioning and/or stabilizing polymers and/or suspending agents, and/or viscosity modifiers, of natural or synthetic origin, especially:

cationic or amphoteric polymers such as cationic guars, cationic polysaccharides, for example PQ-10, cationic synthetic polymers such as PQ-7, and amphoteric synthetic polymers such as PQ-22, PQ-39 and PQ-47, thickeners and/or stabilizers of the acrylate type (including methacrylates), which may be crosslinked, in the form of powders or aqueous dispersions that develop a viscosity by modifying the pH, especially the compounds sold under the brand name Carbopol® by Noveon, and/or compounds whose INCI name is carbomer, acrylate copolymers, and acrylate/C10-30 alkyl acrylate crosspolymers, thickeners and/or stabilizers derived from natural polymers, such as ungrafted guar, which may be partially depolymerized, hydroxypropyl guars; xanthan gum, salts, for example sodium chloride, fragrances, preserving agents, for example the compounds sold under the name Glydant, and parabens, mineral agents other than EGDS-based agents, esters or $C_{10}$-$C_{30}$ and preferably $C_{16}$-$C_{22}$ fatty acids and of polyols or monoalcohols, or ethers of $C_{10}$-$C_{30}$ and preferably $C_{16}$-$C_{22}$ fatty alcohols, other than EGDS, for example distearyl ether, and polyethoxylated and/or polypropoxylated stearates or distearates, for example PEG-3 distearates, PEG/PPG distearates, PEG-200 distearates, PEG-150 distearates and PEG-100 stearates, pH regulators.

A few details regarding certain ingredients that may be used in the formulations are given below.

Cosmetically Acceptable Vector

Any cosmetically acceptable vector that makes it possible to formulate the ampholytic polymer and to obtain the desired form of cosmetic composition, for the intended use, may be used. Various cosmetically acceptable vectors for different types of formulation are known to those skilled in the art.

As examples of cosmetically acceptable vectors, mention may be made of aqueous vectors (comprising water), alcoholic vectors (comprising an alcohol, for example ethanol, isopropanol, ethylene glycol or polyethylene glycols), propylene glycol, and aqueous-alcoholic vectors (comprising a mixture of water and an alcohol, for example ethanol, isopropanol, ethylene glycol or polyethylene glycols). Certain volatile or non-volatile oils may also be used. Mention is made, for example, of fluid silicones, such as cyclopentasiloxane, for example Mirasil CM5 sold by Rhodia.

A person skilled in the art knows how to select the vectors suited to the desired types of formulation and to the intended uses. For example, aqueous vectors are generally used for shampoos or shower gels. A propylene glycol vector may be used in compositions in the form of creams. A cyclomethicone vector may be used for makeup compositions, for example for foundations.

Surfactants for the Formulations

The formulation may comprise at least one surfactant (iv). It may be a mixture of different surfactants. The surfactants may be anionic, cationic, nonionic or amphoteric surfactants, or mixtures or combinations. The surfactants included in the composition preferably comprise at least one anionic or cationic surfactant. The surfactants may also comprise amphoteric (true amphoteric or zwitterionic) surfactants and neutral surfactants (nonionic surfactants). Formulations comprising at least one anionic surfactant and at least one amphoteric surfactant are particularly advantageous, especially for reasons of softness. The total content of surfactants in the composition is generally between 0 and 30% by weight.

For rinse-out or leave-in hair-conditioning formulations, the surfactant is preferably absent or present in an amount of less than 5% by weight, and it may preferably be a cationic surfactant.

For formulations intended for treating the hair, such as shampoos, the surfactant content is advantageously between 10% and 20% by weight. Such formulations may comprise salts, for example sodium or ammonium chloride, advantageously in an amount of less than 3% by weight.

For formulations intended for treating the skin, such as shower gels, the surfactant content is advantageously between 5% and 15% by weight. Such formulations also preferably comprise at least 2% by weight of salts, for example sodium or ammonium chloride.

For hair conditioners, the surfactant content may be less than 5% by weight.

The weight proportion of anionic surfactants relative to the total amount of surfactants is preferably greater than 50% and preferably greater than 70%.

The anionic surfactants may be chosen from the following surfactants:

alkyl ester sulfonates, for example of formula R—CH($SO_3$M)-$CH_2$COOR', or alkyl ester sulfonates, for example of formula R—CH($OSO_3$M)-$CH_2$COOR', in which R represents a $C_8$-$C_{20}$ and preferably $C_{10}$-$C_{16}$ alkyl radical, R' represents a $C_1$-$C_6$ and preferably $C_1$-$C_3$ alkyl radical and M represents an alkaline-earth metal cation, for example sodium, or the ammonium cation. Mention may be made most particularly of methyl ester sulfonates in which the radical R is of $C_{14}$-$C_{16}$;

alkylbenzenesulfonates, more particularly of $C_9$-$C_{20}$, primary or secondary alkylsulfonates, especially of $C_8$-$C_{22}$, and alkylglycerol sulfonates;

alkyl sulfates, for example of formula ROSO$_3$M, in which R represents a $C_{10}$-$C_{24}$ and preferably $C_{12}$-$C_{20}$ alkyl or hydroxyalkyl radical; M represents a cation of the same definition as above;

alkyl ether sulfates, for example of formula RO(OA)$_n$SO$_3$M, in which R represents a $C_{10}$-$C_{24}$ and preferably $C_{12}$-$C_{20}$ alkyl or hydroxyalkyl radical; OA representing an ethoxy or propoxy group; M representing a cation of the same definition as above, n generally ranging from 1 to 4, for instance lauryl ether sulfate with n=2;

alkylamide sulfates, for example of formula RCONHR'OSO$_3$M in which R represents a $C_2$-$C_{22}$ and preferably $C_6$-$C_{20}$ alkyl radical, R' represents a $C_2$-$C_3$ alkyl radical, M representing a cation of the same definition as above, and also polyalkoxylated (ethoxylated and/or propoxylated) derivatives thereof (alkylamido ether sulfates);

salts of saturated or unsaturated fatty acids, for instance of $C_8$-$C_{24}$ and preferably of. $C_{14}$-$C_{20}$ and/or of an alkaline-earth metal cation, N-acyl-N-alkyltaurates, alkylisethionates, alkylsuccinates and alkylsulfosuccinates, alkyl glutamates, sulfosuccinate monoesters or diesters, N-acyl sarcosinates, and polyethoxycarboxylates;

monoester and diester phosphates, for example of the following formula: (RO)$_n$—P(=O)(OM), in which R represents an alkyl, alkylaryl, arylalkyl or aryl radical, optionally polyalkoxylated, x and x' being equal to 1 or 2, on condition that the sum of x and x' is equal to 3, M representing an alkaline-earth metal cation.

The nonionic surfactants may be chosen from the following surfactants:

alkoxylated fatty alcohols, for example laureth-2, laureth-4, laureth-7 or oleth-20;

alkoxylated triglycerides;

alkoxylated fatty acids;

alkoxylated sorbitan esters;

alkoxylated fatty amines;

alkoxylated bis(1-phenylethyl)phenols;

alkoxylated tris(1-phenylethyl)phenols;
alkoxylated alkylphenols;
products resulting from the condensation of ethylene oxide with a hydrophobic compound resulting from the condensation of propylene oxide with propylene glycol, such as the Pluronic products sold by BASF;
products resulting from the condensation of ethylene oxide with the compound resulting from the condensation of propylene oxide with ethylenediamine, such as the Tetronic products sold by BASF;
alkylpolyglycosides, such as those described in U.S. Pat. No. 4,565,647 or alkylglucosides; fatty acid amides, for example of $C_8$-$C_{20}$, especially fatty acid monoalkanolamides, for example cocamide MEA or cocamide MIPA.

The amphoteric surfactants (true amphoteric surfactants comprising an ionic group and a potentially ionic group of opposite charge, or zwitterionic surfactants simultaneously comprising two opposite charges) may be chosen from the following surfactants:
betaines in general, especially carboxybetaines, for example laurylbetaine (Mirataine BB from the company Rhodia) or octylbetaine or cocobetaine (Mirataine BB-FLA from Rhodia); amidoalkylbetaines, for instance cocamidopropylbetaine (CAPB) (Mirataine BDJ from the company Rhodia or Mirataine BET C-30 from Rhodia);
sulfobetaines or sultaines, for instance cocamidopropyl hydroxy sultaine (Mirataine CBS from the company Rhodia);
alkylamphoacetates and alkylamphodiacetates, for instance comprising a cocoyl or lauryl chain (Miranol C2M Conc. NP, C32 and L32 especially, from the company Rhodia);
alkylamphopropionates or alkylamphodipropionates (Miranol C2M SF);
alkyl amphohydroxypropyl sultaines (Miranol CS);
alkylamine oxides, for example lauramine oxide (INCI).

The cationic surfactants may be chosen from the salts of primary, secondary or tertiary fatty amines, optionally polyethoxylated, quaternary ammonium salts such as tetraalkylammonium, alkylamidoalkylammonium, trialkylbenzylammonium, trialkylhydroxyalkylammonium or alkylpyridinium chlorides or bromides, imidazoline derivatives, and amine oxides of cationic nature. An example of a cationic surfactant is cetrimonium chloride or bromide (INCI).

Examples of useful formulations that may be mentioned include:
"sodium" formulations for shampoos typically comprising 12% to 16% by weight of sodium alkyl ether sulfate (for example sodium lauryl ether sulfate "SLES") or a mixture of sodium alkyl ether sulfate and of sodium alkyl sulfate (for example sodium lauryl sulfate "SLS"), 1% to 3% of an amphoteric surfactant (for example cocamidopropylbetaine "CAPB") and 0.5% to 2% of a salt (for example sodium chloride);
"ammonium" formulations for shampoos typically comprising 12% to 16% by weight of ammonium alkyl ether sulfate (for example ammonium lauryl ether sulfate "ALES") or a mixture of ammonium alkyl ether sulfate and of ammonium alkyl sulfate (for example ammonium lauryl sulfate "ALS"), 1% to 3% of an amphoteric surfactant (for example cocamidopropylbetaine "CAPB") and 0 to 2% of a salt (for example ammonium chloride);
"sodium" formulations for shower gels typically comprising 6% to 10% by weight of sodium alkyl ether sulfate (for example sodium lauryl ether sulfate "SLES") or a mixture of sodium alkyl ether sulfate and of sodium alkyl sulfate (for example sodium lauryl sulfate "SLS"), 1% to 3% of an amphoteric surfactant (for example cocamidopropylbetaine "CAPB") and 2% to 4% of a salt (for example sodium chloride);
"ammonium" formulations for shower gels typically comprising 6% to 10% by weight of ammonium alkyl ether sulfate (for example ammonium lauryl ether sulfate "ALES") or a mixture of ammonium alkyl ether sulfate and of ammonium alkyl sulfate (for example ammonium lauryl sulfate "ALS"), 1% to 3% of an amphoteric surfactant (for example cocamidopropylbetaine "CAPB") and 0 to 4% of a salt (for example ammonium chloride).

Other details or advantages may emerge in the light of the non-limiting examples that follow.

EXAMPLES

Example 1

An emulsion having the composition below (weight amount of material per se) is prepared in a stirred tank:

| | |
|---|---|
| EGDS* | 23.50% |
| Water | 47.79% |
| Rhodasurf LA7** (Rhodia) | 14.20% |
| Mirataine BET C-30** (Rhodia) | 12.50% |
| Rhodapex 3N-70** (Rhodia) | 1.24% |
| Miranol Ultra C-32** (Rhodia) | 0.13% |
| Glydant*** | 0.64% |

*85%/15% EGDS/EGMS mixture
**surfactants
***preserving agent

The temperature of the emulsion is 65° C.
Using a piston pump, the emulsion is withdrawn from the tank and introduced at 65° C. into the cooling device described below.

The device is formed of 6 cooling modules in series of tubular pipes, each constituted of a tubular pipe jacketed with a counter-current cooling circuit, and provided with a static mixer. FIG. 1 is a scheme of a module. The cooling fluid flows from right to left in FIG. 1. The emulsion flows from left to right in FIG. 1.

The characteristics of each module are given:
metal tube with an inside diameter of 15 mm,
Kenics static mixer 14 mm in diameter,
length: 500 mm,
working volume: 70 ml,
circular jacket with an outside diameter of 18 mm, for flowing the cooling fluid (water), comprising an inlet and an outlet,
means for measuring temperatures and pressures.

The cooling operation conditions are as follows:
counter-current circulation of cooling water, with an inlet on the last module (relative to the direction of flow) and an outlet on the first module. At the point of connection of the modules, the outlet of the cooling circuit of one module is connected to the inlet of another,
inlet temperature of the cooling water: 50° C.,
flow rate of cooling water: 10 L/hour,
emulsion flow rate 1160 g/hour (residence time: 22 minutes),
temperature of the product at the outlet of the tubular pipe: 50° C.

At the outlet of the flow device, a fluid concentrated ingredient with EGDS-based crystals is obtained, having optical properties (pearlescence) similar to those obtained using a process involving batchwise crystallization in a batch reactor of cooled stirred tank type under far inferior production efficiency conditions (for example expressed as weight of cooled material per hour and optionally per volume occupied).

The invention claimed is:

1. A process for preparing a fluid concentrated ingredient comprising crystals based on a fatty acid ester, comprising the following steps:
    preparing an emulsion comprising water, a compound based on a fatty acid ester, and surfactant(s),
        wherein the temperature of the emulsion is above the melting point of the compound based on the fatty acid ester,
    cooling the emulsion to a temperature below the melting point of the compound to form the crystals,
        wherein said cooling comprises introducing a stream of the emulsion into at least one cooling device,
        further wherein said cooling device is adapted to stir the stream by the stream's own flow,
        wherein the stream flows in at least one flow zone delimited by confinement walls and comprising static obstacles inside said flow zone,
    recovering a stream of a fluid comprising the crystals and the surfactant(s) downstream of the cooling device,
    optionally cooling the stream again,
    optionally adding other compounds to the fluid, diluting the fluid, and/or mixing the fluid, and
    recovering the fluid concentrated ingredient.

2. The process of claim 1, wherein cooling the emulsion comprises adding a chilling fluid to the stream upstream of the cooling device and/or in the cooling device.

3. The process of claim 1, wherein cooling the emulsion comprises adding a seeding fluid comprising crystals based on a fatty acid ester to the stream.

4. The process of claim 1, wherein said cooling device comprises a cooling fluid in a cooling circuit,
    further wherein the cooling circuit comprises walls, at least a part of which are in contact with the stream.

5. The process of claim 4, wherein the cooling circuit is located inside the flow zone and comprises an obstacle to flow of the stream.

6. The process of claim 4, wherein the cooling circuit is located outside the flow zone.

7. The process of claim 6, wherein the flow zone comprises at least one tubular pipe comprising confinement walls,
    wherein said flow zone comprises a static mixer, and at least part of the confinement walls comprise a common wall with at least a part of the cooling circuit.

8. The process of claim 7, wherein the cooling device comprises a jacketed tube exchanger comprising a tubular circuit inside of which is located a tubular pipe in which the stream flows.

9. The process of claim 4, wherein the at least one cooling device comprises a tube exchanger, a multitube exchanger, a coil exchanger, a plate exchanger, an exchangers of Sulzer® Mixer Reactor (SMR®) type, or a combination thereof.

10. The process of claim 1, wherein the temperature of the stream before cooling is greater than or equal to 1° C. higher than the melting point of the compound based on the fatty acid ester.

11. The process of claim 1, wherein said cooling comprises cooling the emulsion at least 5° C.

12. The process of claim 1, wherein the fatty acid ester comprises an ester of a fatty acid with a diol or a polyol of formula:

[R—COO—]$_x$-A-[OH]$_y$ wherein:
R comprises a saturated or unsaturated, linear or branched $C_{11}$-$C_{12}$ hydrocarbon-based group,
A comprises a hydrocarbon-based group, optionally interrupted with one or more heteroatoms, of valency x+y,
x is an average number ranging from 1 to 5,
y is an average number ranging from 0 to 5, and
x+y is an average number ranging from 1 to 10.

13. The process of claim 12, wherein the group A comprises:

—(CH$_2$)$_z$-[EO]$_n$—[PO]$_m$—(CH$_2$)$_z$— wherein:
z, which may be identical or different, is an integer from 1 to 10,
EO is an optional ethylene oxide group,
n is an average number ranging from 0 to 100,
PO is an optional propylene oxide group, and
m is an average number ranging from 0 and 100.

14. The process of claim 1, wherein the fatty acid ester is based on ethylene glycol distearate (EGDS).

15. The process of claim 1, wherein the amounts of compound based on fatty acid ester and surfactant(s) are such that the step of recovering the stream of fluid comprising the crystals and the surfactant(s) downstream of the cooling device comprises recovering:
    at least 5% by weight of fatty acid ester, and
    at least 2.5% by weight of surfactant(s).

16. A foaming composition comprising the fluid concentrated ingredient of claim 1,
    wherein the amount of the crystals in the foaming composition ranges from 1% to 4% by weight.

17. The foaming composition of claim 16, wherein said foaming composition comprises a cosmetic formulation or a household maintenance formulation.

* * * * *

UNITED STATES PATENT AND TRADEMARK OFFICE
CERTIFICATE OF CORRECTION

PATENT NO. : 8,536,356 B2 Page 1 of 1
APPLICATION NO. : 12/937926
DATED : September 17, 2013
INVENTOR(S) : Carvin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 302 days.

Signed and Sealed this
Fifteenth Day of September, 2015

Michelle K. Lee
*Director of the United States Patent and Trademark Office*